United States Patent
Nord et al.

(10) Patent No.: US 6,302,582 B1
(45) Date of Patent: Oct. 16, 2001

(54) SPINE PHANTOM SIMULATING CORTICAL AND TRABECULAR BONE FOR CALIBRATION OF DUAL ENERGY X-RAY BONE DENSITOMETERS

(75) Inventors: Russell H. Nord, Fort Atkinson, WI (US); Colin G. Miller, Churchville, PA (US)

(73) Assignee: Bio-Imaging Technologies, Inc., West Trenton, NJ (US)

( * ) Notice: Subject to any disclaimer, the term of this patent is extended or adjusted under 35 U.S.C. 154(b) by 0 days.

(21) Appl. No.: 09/468,030

(22) Filed: Dec. 20, 1999

Related U.S. Application Data

(60) Provisional application No. 60/113,318, filed on Dec. 22, 1998.

(51) Int. Cl.$^7$ ..................................................... G01D 18/00
(52) U.S. Cl. ............................................. 378/207; 378/18
(58) Field of Search ................................. 378/207, 18, 56

(56) References Cited

U.S. PATENT DOCUMENTS

| | | | |
|---|---|---|---|
| 5,235,628 | * | 8/1993 | Kalender ............................... 378/207 |
| 5,335,260 | * | 8/1994 | Arnold ................................... 378/207 |
| 5,481,587 | * | 1/1996 | Mazess ................................... 378/207 |

* cited by examiner

*Primary Examiner*—Robert H. Kim
*Assistant Examiner*—Courtney Thomas
(74) *Attorney, Agent, or Firm*—Quarles & Brady LLP

(57) ABSTRACT

Disclosed herein is a spine phantom for calibrating a dual energy x-ray attenuation measurement device for measuring vertebral bone density. Simplified construction of the phantom is made possible by equating the density variations in the three dimensionally complex and inhomogeneous spine as a set of easily machined flat surfaces of different thicknesses. In particular, the spine phantom includes a vertebra-simulating body having a base surface perpendicular to the x-ray beam of the measurement device and defining an intervertebral section, a composite bone section and cortical wall sections. These sections each extend to planes of different heights from the base surface, so as to simulate cartilage, cortical and tabecular bone, and cortical bone wall regions of a human spine, respectively. The spine phantom of the present invention can include multiple vertebra-simulating bodies simulating a range of vertebra types and densities. Moreover, the vertebra-simulating bodies may be embedded in an acrylic block lined with a vinyl layer so as to simulate a human spine surrounded by soft tissue.

19 Claims, 3 Drawing Sheets

SPINE PHANTOM SIMULATING CORTICAL AND TRABECULAR BONE FOR CALIBRATION OF DUAL ENERGY X-RAY BONE DENSITOMETERS

CROSS-REFERENCE TO RELATED APPLICATIONS

This application claims the benefit of U.S. provisional application Ser. No. 60/113,318, filed Dec. 22, 1998.

STATEMENT REGARDING FEDERALLY SPONSORED RESEARCH OR DEVELOPMENT

Not applicable

BACKGROUND OF THE INVENTION

The present invention relates to phantoms for x-ray machines and the like, and in particular, to a phantom providing calibration for dual energy x-ray equipment used in bone density measurement.

The absorption of x-rays by material is dependent on two independent atomic properties of the material, the Compton scattering of x-rays by the material and photoelectric absorption. The relative proportion of these two types of absorption is different for different materials and varies as a function of frequency. Accordingly, measurements of the material at two x-ray energies (generally corresponding to different x-ray frequencies) can reveal information about the properties of the material.

Dual energy measurements can be used to measure relative proportions of any two basis materials making up the material. A principal use of this phenomenon is in the measurement of the basis materials of bone and soft tissue to provide an in vivo measurement of bone mass. Lunar Corporation, the assignee of the present application, manufactures a number of dual energy x-ray machines suitable for this purpose as described in the following U.S. patents hereby incorporated by reference: U.S. Pat. Nos. 5,253,282; 5,228,068; 5,287,546; 5,291,537; 5,305,368; 5,306,306; 5,408,439; 5,485,492; 5,509,042; 5,533,080; 5,533,084; 5,577,089 and 5,673,298.

In making bone density measurements, it is important that repeatable quantitative results be produced. For this reason, it is necessary that a machine be calibrated frequently to prevent drifting of the measurements over time. In the case where multiple machines may be used in a study, each machine must be cross-calibrated to identify inconsistencies among the machines. Critical too, for bone density measurements, is that a similar region of the bone be examined among patients or for an individual patient over different scans. Finally, when making calibrations for bone density, it is important that they show the same range of readings for different samples.

What is needed is a simple and accurate phantom that can be used with dual energy densitometers to monitor its calibration performance over time, as well as to provide cross-calibration of multiple densitometers, by simulating measurement of the irregular and inhomogeneous spine.

BRIEF SUMMARY OF THE INVENTION

The present invention provides a phantom simulating a range of vertebra types and densities, curvature of the lateral vertebral walls, intervertebral cartilage, and the cortical and trabecular regions of the vertebra. Simplified construction of the phantom is made possible by equating the density variations in the three dimensionally complex and inhomogeneous spine as a set of easily machined flat surfaces of different thicknesses.

In particular, the present invention provides a spine phantom for calibrating a dual energy x-ray attenuation measurement device for measuring vertebral bone density. The spine phantom includes a vertebra-simulating body having a base surface extending in longitudinal and transverse directions to support the vertebra-simulating body substantially perpendicular to an x-ray beam of the measurement device. The vertebra-simulating body defines an intervertebral section, a composite bone section and cortical wall sections. These sections each extend to respective first, second and third planes of different heights from the base surface, so as to simulate the x-ray attenuation characteristics of cartilage, cortical and trabecular bone, and cortical bone wall regions of a human spine, respectively.

The spine phantom can include a plurality of such vertebra-simulating bodies, each having an intervertebral section, composite bone section and cortical wall sections. The vertebra-simulating bodies are aligned and joined at the intervertebral sections to define voids between the composite bone sections of each body. The composite bone sections and the cortical wall sections of each vertebra-simulating body extend to a different height from the base surface, such that each vertebral body has second and third planes at unique heights from the base surface. This variation in height between the vertebra-simulating bodies simulates various human vertebral bone density values, ranging from that of a healthy human spine to that of an osteoporotic spine. Additionally, the distance between the second and third planes is different for each vertebra-simulating body and the composite bone section of each body has a plateau surface at its second plane of a unique size, simulates vertebra of different overall bone masses. The spine phantom may also include one or more calibration blocks extending to a prescribed height above the base surface.

In one aspect of the invention, the vertebra-simulating bodies may be a homogeneous material, preferably, calcium hydroxyapatite. In another aspect, the cortical wall sections define concave outer surfaces. These surfaces provide a means for testing the edge detection algorithms of x-ray attenuation measurement devices and can be used by certain devices for locating a particular spinal region of interest.

In another aspect of the present invention, the spine phantom may include a preferably acrylic block into which the vertebral body is embedded. A sheet layer, preferably made of polyvinylchloride, can also be affixed to the block that attenuates x-rays differently than the block such that the sheet layer and block together have x-ray attenuation characteristics simulating human soft tissue. So that when a vertebra-simulating bodies are disposed in the block, the spine phantom simulates a human vertebra surrounded by soft tissue.

In yet another aspect, the spine phantom can be disposed in a suitable carrying case or bag for transport between x-ray attenuation devices needing calibration as well as for safe storage. Preferably, the carrying case is made of a suitable x-ray translucent material such that the spine phantom may be scanned without being removed from its case.

Thus, the present invention provides a calibration phantom simulating a human spine at various spinal regions and in various states of bone decay. The phantom is made from a homogenous material and has easily machinable surfaces. These and still other advantages of the present invention will be apparent from the description of the preferred embodiments which follow.

DETAILED DESCRIPTION OF THE INVENTION

Figure 1:
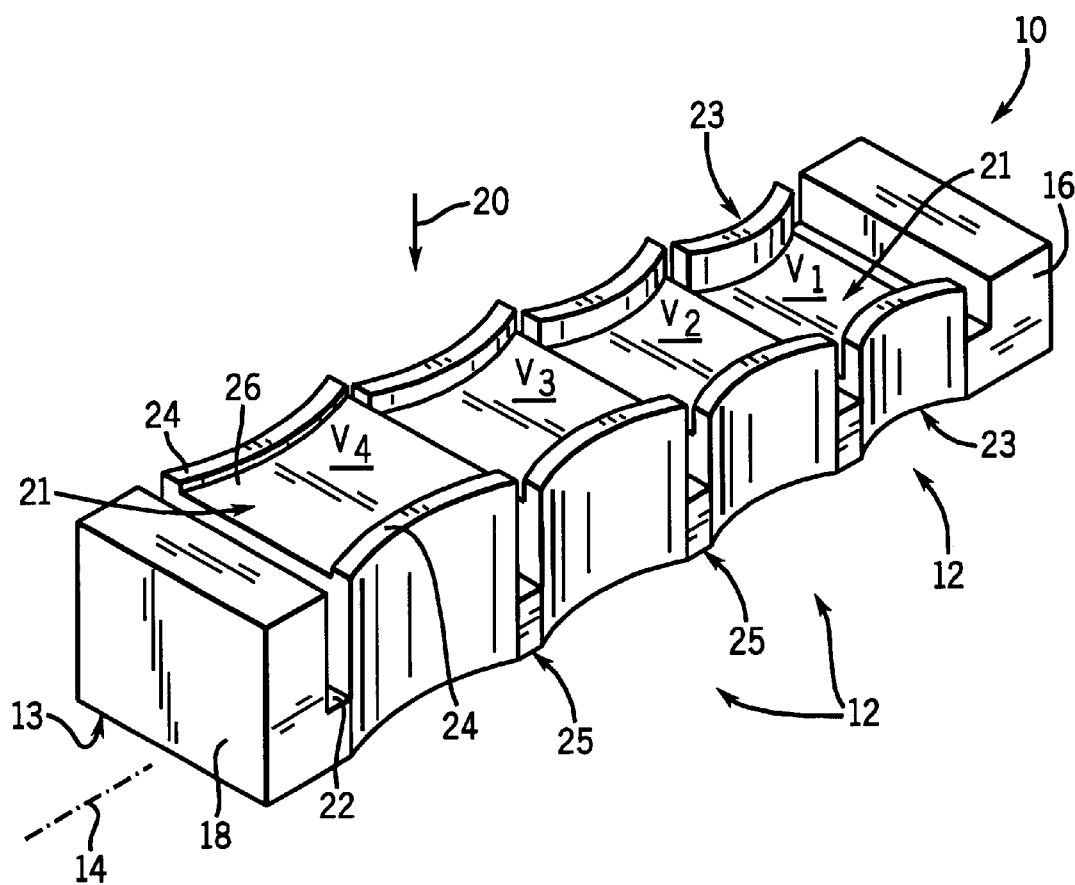
FIG. 1 is perspective view of the phantom of the present invention showing four simulated vertebral bodies flanked by constant thickness calibration blocks as may be machined from hydroxyapatite.

Referring now to FIG. 1, a phantom 10 of the present design for calibrating x-ray attenuation measurement devices, such as dual energy x-ray bone densitometers includes generally four vertebral bodies 12 designated $V_1$–$V_4$ having a bottom base surface 13 and arranged along a spinal axis 14 in a manner that simulates the spine of the human being. Radiation may be directed at the phantom 10 along a radiation axis 20 perpendicular to the spinal axis 14.

Figure 2:
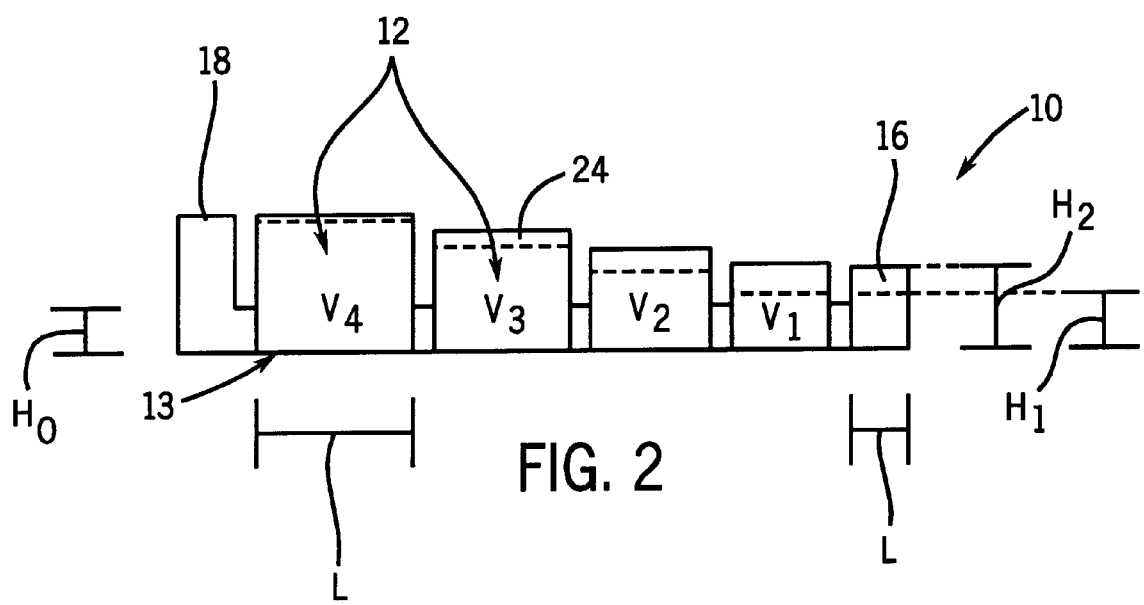
FIG. 2 is a front elevational view of the phantom of FIG. 1.
Figure 3:
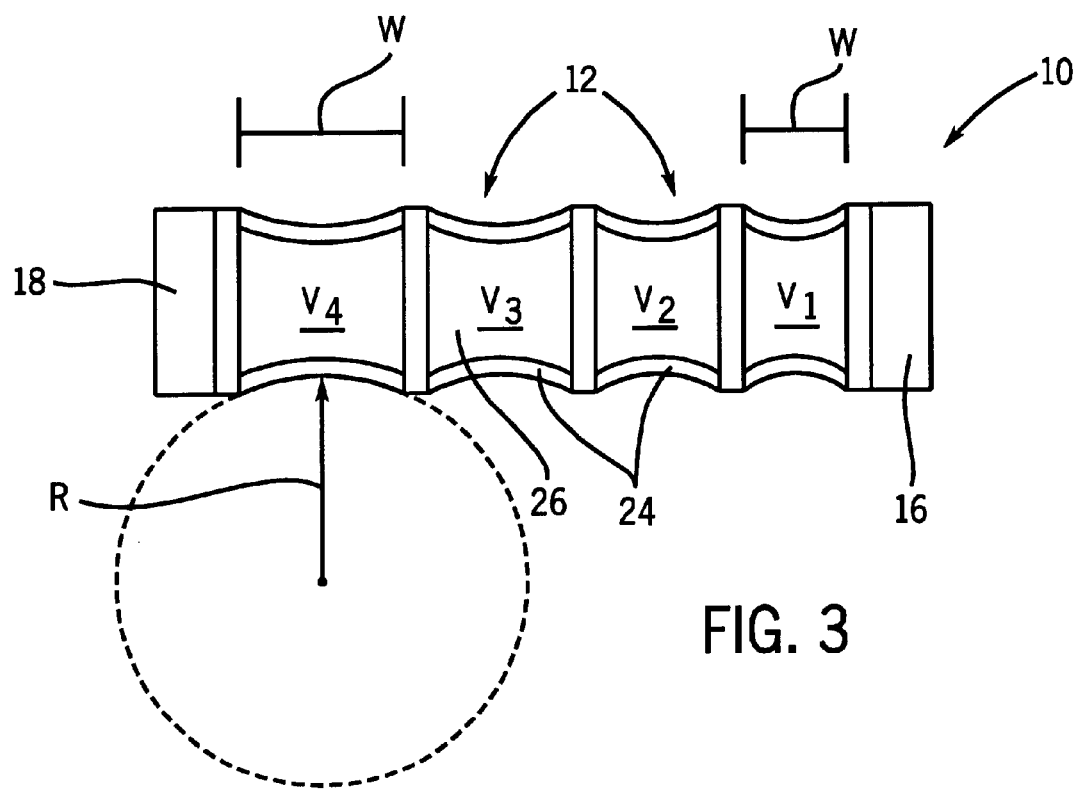
FIG. 3 is a top plan view of the phantom of FIG. 1.

Referring now also to FIGS. 2 and 3, the vertebral bodies 12 flanked on a superior side by calibration block 16 (adjacent to vertebral body $V_1$) and on an inferior side by calibration block 18 (adjacent to vertebral body $V_4$). The calibration blocks 16 and 18 are generally equal in width to the vertebral bodies 12 (nominally 1.555 inches), as measured perpendicular to the axis 14, but having different heights $H_1$ as measured along radiation axis 20 as shown in Table I below. The vertebral bodies 12 have progressively greater length L measured along axis 14 and progressively greater heights $H_1$ measured along radiation axis 20 as one moves from block 16 to block 18 along the phantom 10 as also shown in Table I. The vertebral bodies $V_1$–$V_4$ simulate vertebral bone density at various stages of bone decay, preferably ranging from a healthy human adult (V1) to an osteoporotic human adult. The vertebral bodies may be easily machined as needed to simulate other degrees of bone density.

Each vertebral body 12 includes a composite bone section 21, having x-ray attenuation characteristics simulating that of the trabecular and cortical bone sections of human vertebrae. Each composite bone section 21 is flanked by cortical wall sections 23 having x-ray attenuation characteristics simulating that of the higher density cortical walls of human vertebrae. The left and right lateral edges of the cortical wall sections 23 are concave inward, each concavity following a surface of a cylinder whose axis is aligned with radiation axis 20 and which is positioned adjacent to the left or right lateral edges of the cortical wall sections 23. For different vertebral bodies 12 ($V_1$–$V_4$) the defining cylinders having progressively smaller radiuses to conform with the changes in lengths L as also indicated in Table 1. The cylindrical concavity can be cut easily by conventional machining techniques. The concave surfaces can be used to test the edge detection algorithms of the measurement devices.

Upwardly extending rails 24 are formed at the cortical wall sections 23 at the left and right lateral edges of the vertebral bodies 12, the rails 24 conforming to the concave shape of the radiused lateral edges and extending upward above the heights $H_1$ the composite bone sections of their respective vertebral bodies 12. The rails 24 for each vertebral body 12 have a width measured across the spinal axis 14 perpendicular to the radiation axis 20 of 0.19 inches and separated from each other in this same direction by a plateau 26 having the heights $H_1$ vertebral body 12 previously described. The rails 24 serve to increase the apparent density at the edge of the vertebral bodies 12 as would be the case in a real vertebra as a result of the higher density of the cortical bone over the trabecular bone. The absolute height $H_2$ of these ridges for each vertebral body 12 is shown in Table 1.

The vertebral bodies 12 are separated from each other and from the blocks 16 and 18 by grooves 22 extending down to an intervertebral section 25 simulating the x-ray attenuation characteristics of the lower density intervertebral material such as cartilage. The height of the material within each groove ($H_0$) is 0.4 inches. The end blocks 18 and 16 having no rails 24 simply have a plateau height $H_1$.

TABLE 1

| | L | R | $H_0$ | $H_1$ | $H_2$ |
|---|---|---|---|---|---|
| Superior End Block 16 | 0.500 | — | 0.4 | 0.711 | — |
| V1 | 0.833 | 0.638 | 0.4 | 0.459 | 0.711 |
| V2 | 1.041 | 0.810 | 0.4 | 0.669 | 0.868 |
| V3 | 1.182 | 0.966 | 0.4 | 0.899 | 1.028 |
| V4 | 1.371 | 1.500 | 0.4 | 1.140 | 1.200 |
| Inferior End Block 18 | 0.500 | — | — | 1.2 | — |

All dimensions in Table 1 are in inches.

Figure 4:
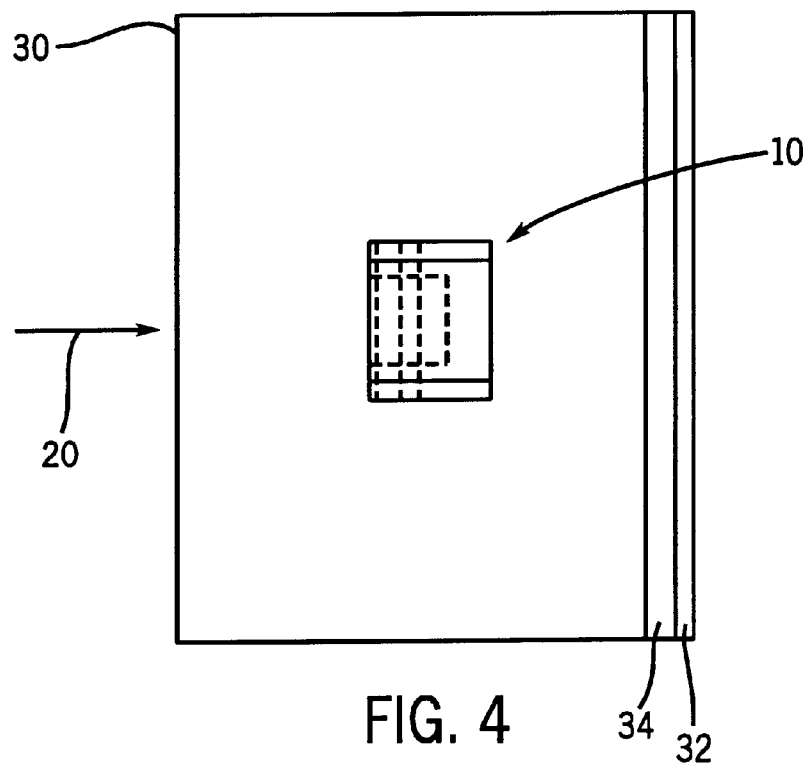
FIG. 4 is a top plan view of the phantom of FIG. 1 embedded in a block simulating soft tissue.
Figure 5:
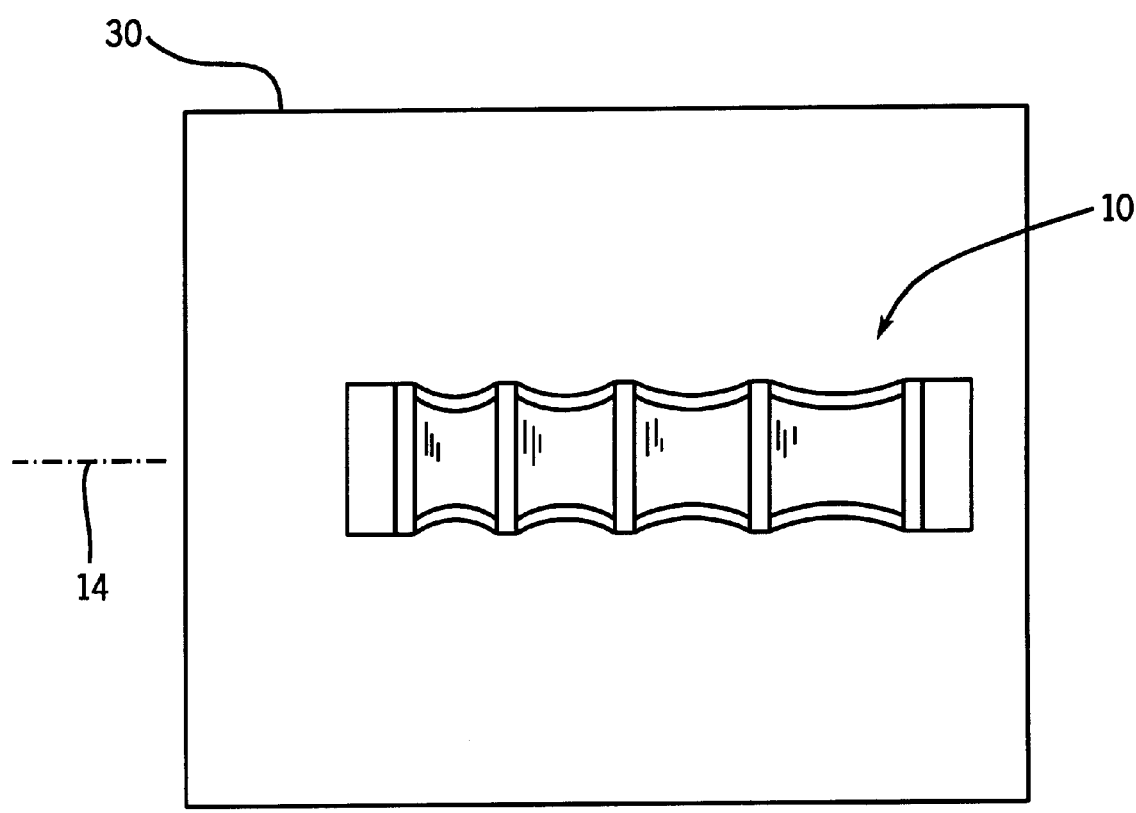
FIG. 5 is a side elevational view of the phantom and block of FIG. 4.

Referring now to FIGS. 4 and 5, the phantom 10 may be embedded in an acrylic block 30 simulating soft tissue surrounding the spine and having a dimension along radiation axis 20 of approximately 5.7 inches and a dimension perpendicular to axis 14 and 20 of 7.5 inches and a dimension along axis 14 of 8.66 inches. A gray polyvinylchloride (PVC) sheet of 0.125 inches in height may be laminated to the bottom of the acrylic block 30 extending perpendicularly to the radiation axis 20 so as to correct absorption of the block 30 to more accurately be that of soft tissue and make capture between it and block 30 and opaque black acrylic sheet 34 may be sandwiched between sheet 32 and the block 30 to provide greater visibility of the phantom during positioning operations.

The phantom material may be a calcium hydroxyapatite (CHA) having a density of 0.14 to 0.155 grams per cubic centimeter embedded in a polymer matrix such as epoxy. However, it will be understood to those of ordinary skill in the art that other materials may be used and that these densities may be varied as required. The PVC sheet may be obtained commercially from Vycom located at Moosic, Pennsylvania and the CHA obtained from Computerized Imaging References Systems, Inc. located at Norfolk, Va.

The present invention may include other aspects not specifically delineated in the aforementioned preferred embodiments. For example, the spine phantom may include only a single vertebral body with or without the calibration blocks. Or, the spine phantom, with or without the arcylic block, can be disposed in a suitable carrying case or bag (not shown) that is made of a suitable x-ray translucent material, i.e., a material which does not attenuate x-rays. In this way, the spine phantom can be carried to a examination station and scanned without being removed from the case.

Thus, the above in no way is intended to limit the scope of the invention. Accordingly, in order to apprise the public of the full scope of the present invention, reference must be made to the following claims.

We claim:

1. A spine phantom for calibrating a dual energy x-ray attenuation measurement device for measuring vertebral bone density, the spine phantom comprising:
   a vertebra-simulating body having a base surface extending in longitudinal and transverse directions to support the vertebra-simulating body substantially perpendicular to an x-ray beam of the measurement device, the vertebra-simulating body defining:
      an intervertebral section extending from a longitudinal end of the base surface upward to a first height, the intervertebral section simulating the x-ray attenuation characteristics of cartilage disposed between vertebrae of a human spine;
      a composite bone section adjacent to the intervertebral section and extending from the base surface upward to a second height greater than the first height, the composite bone section simulating the x-ray attenuation characteristics of trabecular and cortical bone regions of human vertebrae; and
      cortical wall sections extending upward from the base surface to a third height greater than the second height, the cortical wall sections transversely flanking the composite bone section and simulating the x-ray attenuation characteristics of cortical bone walls of human vertebrae;
   whereby different x-ray attenuation characteristics of the intervertebral, composite bone and cortical wall sections are effected by the sections being at different first, second and third heights, respectively.

2. The spine phantom of claim 1, wherein the vertebra-simulating body is a homogeneous material.

3. The spine phantom of claim 2, wherein the material is a calcium hydroxyapatite.

4. The spine phantom of claim 1, wherein the cortical wall sections define concave outer surfaces.

5. The spine phantom of claim 1, further comprising a block into which the vertebra-simulating body is embedded.

6. The spine phantom of claim 5, further comprising a sheet layer affixed to the block, the sheet layer attenuating x-rays differently than the block, the sheet layer and block together having x-ray attenuation characteristics simulating human soft tissue.

7. The spine phantom of claim 6, wherein the block is acrylic and the sheet layer is a vinyl-based substance.

8. The spine phantom of claim 1, further comprising a plurality of vertebra-simulating bodies, each having an intervertebral section, composite bone section and cortical wall sections, aligned and joined at the intervertebral sections so as to define voids between the composite bone sections of each of the plurality of vertebra-simulating bodies.

9. The spine phantom of claim 8, wherein the composite bone sections and the cortical wall sections of each vertebra-simulating body extend to a different height from the base surface, such that each vertebra-simulating body has second and third planes at unique heights from the base surface, whereby the variation in height between the plurality of vertebra-simulating bodies simulates various human vertebral bone density values.

10. The spine phantom of claim 9, wherein the distance between the second and third planes is different for each of the plurality of vertebra-simulating bodies.

11. The spine of claim 9, wherein the composite bone section of each of the plurality of vertebra-simulating bodies has a plateau surface at its second plane of a unique size, simulating various total vertebral masses.

12. The spine phantom of claim 9, wherein the various human vertebral bone density values range from that of a healthy human spine to an osteoporotic human spine.

13. The spine of claim 8, further comprising at least one calibration block extending to a prescribed height above the base surface.

14. The spine phantom of claim 8, wherein the plurality of vertebra-simulating bodies are made of a homogeneous material.

15. The spine phantom of claim 14, wherein the material is a calcium hydroxyapatite.

16. The spine phantom of claim 8, further comprising a block into which the plurality of vertebra-simulating bodies are embedded.

17. The spine phantom of claim 16, further comprising a sheet layer affixed to the block, the sheet layer attenuating x-rays differently than the block, the sheet layer and block together having x-ray attenuation characteristics simulating soft tissue surrounding a human spine.

18. The spine phantom of claim 17, wherein the block is acrylic and the sheet layer is a vinyl-based substance.

19. The spine phantom of claim 1, further comprising an x-ray translucent case in which the vertebra-simulating body is disposed.

* * * * *